(12) United States Patent
Orr et al.

(10) Patent No.: US 8,232,396 B2
(45) Date of Patent: Jul. 31, 2012

(54) PROCESSES FOR THE SYNTHESIS OF OPIATES ALKALOIDS WITH REDUCED IMPURITY FORMATION

(75) Inventors: Brian Orr, Ofallon, MO (US); Miranda Steele, St. Louis, MO (US)

(73) Assignee: Mallinckrodt LLC, Hazelwood, MO (US)

( * ) Notice: Subject to any disclaimer, the term of this patent is extended or adjusted under 35 U.S.C. 154(b) by 445 days.

(21) Appl. No.: 12/586,841

(22) Filed: Sep. 29, 2009

(65) Prior Publication Data

US 2010/0081813 A1    Apr. 1, 2010

Related U.S. Application Data

(60) Provisional application No. 61/194,686, filed on Sep. 30, 2008.

(51) Int. Cl.
*C07D 489/12* (2006.01)
*C07D 489/02* (2006.01)

(52) U.S. Cl. .......................................... 546/39; 546/44
(58) Field of Classification Search .................... 546/39, 546/44
See application file for complete search history.

(56) References Cited

FOREIGN PATENT DOCUMENTS

| EP | 1 439 179 | 7/2004 |
|---|---|---|
| GB | 902659 | 8/1962 |
| WO | WO 2007/081506 | 7/2007 |

OTHER PUBLICATIONS

Bentley et al., "Novel Analgesics and Molecular Rearrangements in the Morphine-Thebaine . . . ", Journal of the American Chemical Society, 89(13), 1976, pp. 3267-3273.
Uff et al., "NMR Spectra and Stereochemistry of some 7-Substituted 6,14-Bridged Thebaine Derivatives", Magnetic Resonance in Chemistry, 23(6), 2005, pp. 454-459.

*Primary Examiner* — Charanjit Aulakh

(57) ABSTRACT

The invention provides processes for the production of opiate alkaloids. In particular, the present invention provides processes for the formation of opiate alkaloids that minimizes the formation of impurities.

20 Claims, 2 Drawing Sheets

PROCESSES FOR THE SYNTHESIS OF OPIATES ALKALOIDS WITH REDUCED IMPURITY FORMATION

CROSS REFERENCE TO RELATED APPLICATIONS

This application claims the benefit of the filing date of U.S. Provisional Application Serial no. 61/194,686, filed Sep. 30, 2008, entitled "Processes for the synthesis of opiate alkaloids with reduced impurity formation" which is incorporated herein in their entirety.

FIELD OF THE INVENTION

The present invention generally relates to processes for the synthesis of opiate alkaloids. In particular, the present invention provides processes for the formation of opiate alkaloids that minimizes the formation of impurities.

BACKGROUND OF THE INVENTION

Thebaine is an opiate alkaloid. While thebaine is not used therapeutically itself, it can be converted industrially into a variety of therapeutically important opiate alkaloids including oxycodone, oxymorphone, nalbuphine, naloxone, naltrexone, diprenorphine, buprenorphine and etorphine. Buprenorphine, for example, is a thebaine derivative with powerful analgesia approximately twenty-five to forty times as potent as morphine, and is indicated for the treatment of moderate to severe chronic pain or for pre-operative analgesia.

Buprenorphine is made via a synthetic route that starts with the conversion of thebaine to 6,14-endo-etheno-7α-acetyltetrahydro-thebaine. In particular, thebaine has been reacted with a dienophile (e.g., methyl vinyl ketone) in the presence of an alcohol to produce the Diels Alder product 6,14-endo-etheno-7α-acetyltetrahydro-thebaine (K. W. Bentley and D. G. Hardy, J. Am. Chem. Soc., 1967, 89 (13), 3267-3273. More precisely, the Diels Alder product is a mixture of two epimers: 6,14-endo-etheno-7α-acetyltetrahydro-thebaine and 6,14-endo-etheno-7βacetyltetrahydro-thebaine. The reported ratio of the 7-α epimer to the 7-β epimer formed by the aforementioned process is 98.44:1.56, respectively. Of these two epimers, the 7-α epimer is an important early intermediate used to produce buprenophine, and the 7β epimer is an impurity that results in the formation of unwanted side compounds. For example, if the 7-β epimer isn't isolated it carries on in the buprenorphine synthesis to produce 7-β-buprenorphine, an impurity, at levels higher than currently prescribed guidelines established by the International Conference on Harmonisation of Technical Requirements for Registration of Pharmaceuticals for Human Use (ICH). As such, even trace amounts of the 7-β epimer are undesirable in a final product. So while the traditional Diels Alder conversion of thebaine to 6,14-endo-etheno-7α-acetyltetrahydro-thebaine results in the formation of a relatively high yield of the Diels Alder product, it also produces unacceptably high levels of the 7-β epimer in the key intermediate. A need therefore exists for a process that provides a high yield of 6,14-endo-etheno-7α-acetyltetrahydro-thebaine while minimizing the formation of 6,14-endo-etheno-7β-acetyltetrahydro-thebaine.

SUMMARY OF THE INVENTION

The present invention provides a synthetic route for the production of one or more alkaloid compounds in a one-pot process via a Diels Alder reaction that utilizes a solvent system comprising water and a solvent that is miscible in water to reduce the formation of impurities, such as the 7-β epimer of 6,14-endo-etheno-7-acetyltetrahydro-thebaine. The synthetic route may be utilized to produce a variety of compounds, including intermediate compounds used in the production of opiate alkaloids.

Briefly, therefore, in one aspect the present invention encompasses a process for the preparation of a compound comprising Formula (II) containing low 7-β epimer levels:

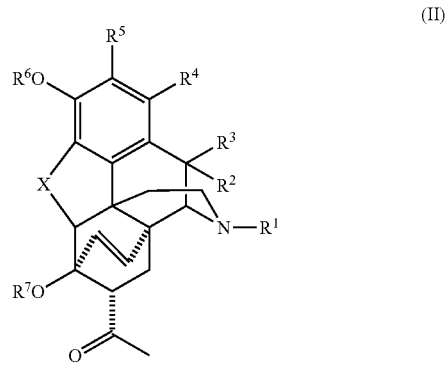

(II)

The process comprises forming a reaction mixture by combining a compound of Formula (I), with a dienophile and a solvent system comprising water, the compound of Formula (I) comprising:

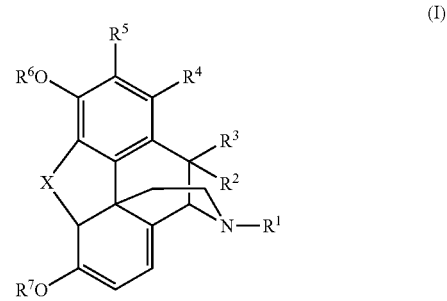

(I)

The reaction mixture is heated for a period of time sufficient to allow for the formation of a compound comprising Formula (II). For each of the compounds comprising Formula (I) or (II) the variables stand for the following:

$R^1$ and $R^8$ are independently selected from the group consisting of hydrocarbyl and substituted hydrocarbyl;

$R^2$ and $R^3$ are independently selected from the group hydrogen, hydrocarbyl and substituted hydrocarbyl;

$R^4$ and $R^5$ are independently selected from the group consisting of hydrogen, hydrocarbyl, substituted hydrocarbyl, halogen, $\{-\}OH$, $\{-\}NH_2$, $\{-\}SH$, $\{-\}SR^8$, and $\{-\}OR^8$;

$R^6$ and $R^7$ are independently selected from the group consisting of hydrogen, a protecting group, hydrocarbyl, and substituted hydrocarbyl; and X is a heteroatom.

Yet another aspect of the invention provides a process for the preparation of a compound comprising Formula (IIa):

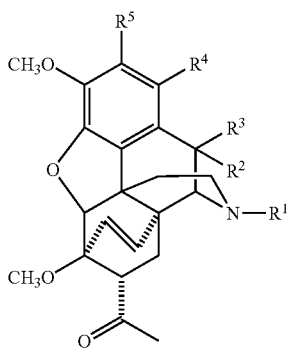

(IIa)

The process comprises forming a reaction mixture by combining a compound of Formula (Ia), with a dienophile and a solvent system comprising water, the compound of Formula (Ia) comprising:

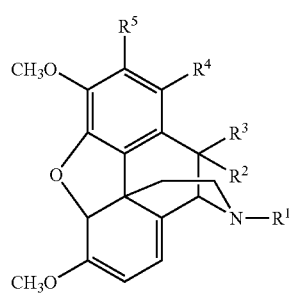

(Ia)

The reaction mixture is heated for a period of time sufficient to allow for the formation of a compound comprising Formula (IIa). For each of the compounds comprising Formula (Ia) or (IIa) the variables stand for the following:

$R^1$ and $R^8$ are independently selected from the group consisting of hydrocarbyl and substituted hydrocarbyl;

$R^2$ and $R^3$ are independently selected from the group hydrogen, hydrocarbyl and substituted hydrocarbyl; and $R^4$ and $R^5$ are independently selected from the group consisting of hydrogen, hydrocarbyl, substituted hydrocarbyl, halogen, {—}OH, {—}NH$_2$, {—}SH, NSW, and {—}OR$^8$.

Another aspect of the invention encompasses a process for the preparation of a compound comprising Formula (IIb):

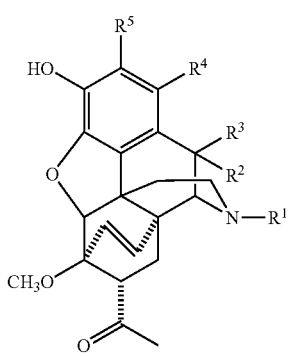

(IIb)

The process comprises forming a reaction mixture by combining a compound of Formula (Ib), with a dienophile and a solvent system comprising water, the compound of Formula (Ib) comprising:

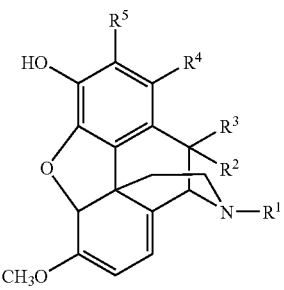

(Ib)

The reaction mixture is heated for a period of time sufficient to allow for the formation of a compound comprising Formula (IIb). For each of the compounds comprising Formula (Ib) or (IIb) the variables stand for the following:

$R^1$ and $R^8$ are independently selected from the group consisting of hydrocarbyl and substituted hydrocarbyl;

$R^2$ and $R^3$ are independently selected from the group hydrogen, hydrocarbyl and substituted hydrocarbyl; and $R^4$ and $R^5$ are independently selected from the group consisting of hydrogen, hydrocarbyl, substituted hydrocarbyl, halogen, {—}OH, {—}NH$_2$, {—}SH, {—}SR$^8$, and {—}OR$^8$.

Other features and iterations are described in more detail below.

DETAILED DESCRIPTION OF THE INVENTION

Figure 1:
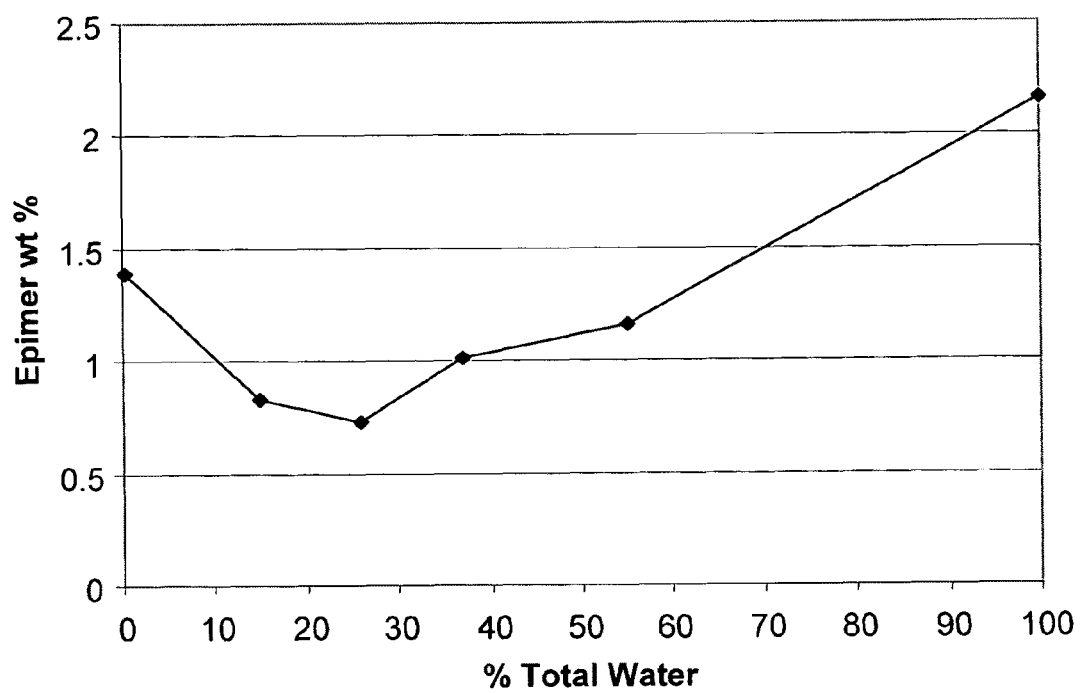
FIG. 1 depicts a graph that illustrates the correlation between the amount of 7-β epimer formed as the percentage (v/v) of water increases during the reaction of thebaine with methyl vinyl ketone to produce 6,14-endo-etheno-7α-acetyltetrahydro-thebaine. The graph depicts use of six different amounts of water, namely 0% (v/v), 15% (v/v), 26% (v/v); 37% (v/v), 55% (v/v), and 100% (v/v). As shown in the graph, 0% (v/v) of water results in the formation of 1.401% by weight of the 7-β epimer, 15% (v/v) of water results in the formation of 0.828% by weight of the 7-β epimer, 26% (v/v) of water results in the formation of 0.724% by weight of the 7-β epimer, 37% (v/v) of water results in the formation of 1.010% by weight of the 7-β epimer, 55% (v/v) of water results in the formation of 1.155% by weight of the 7-β epimer, and 100% (v/v) of water results in the formation of 2.160% by weight of the 7-β epimer. The reactions were conducted in accordance with the procedures described in Example 1.
Figure 2:
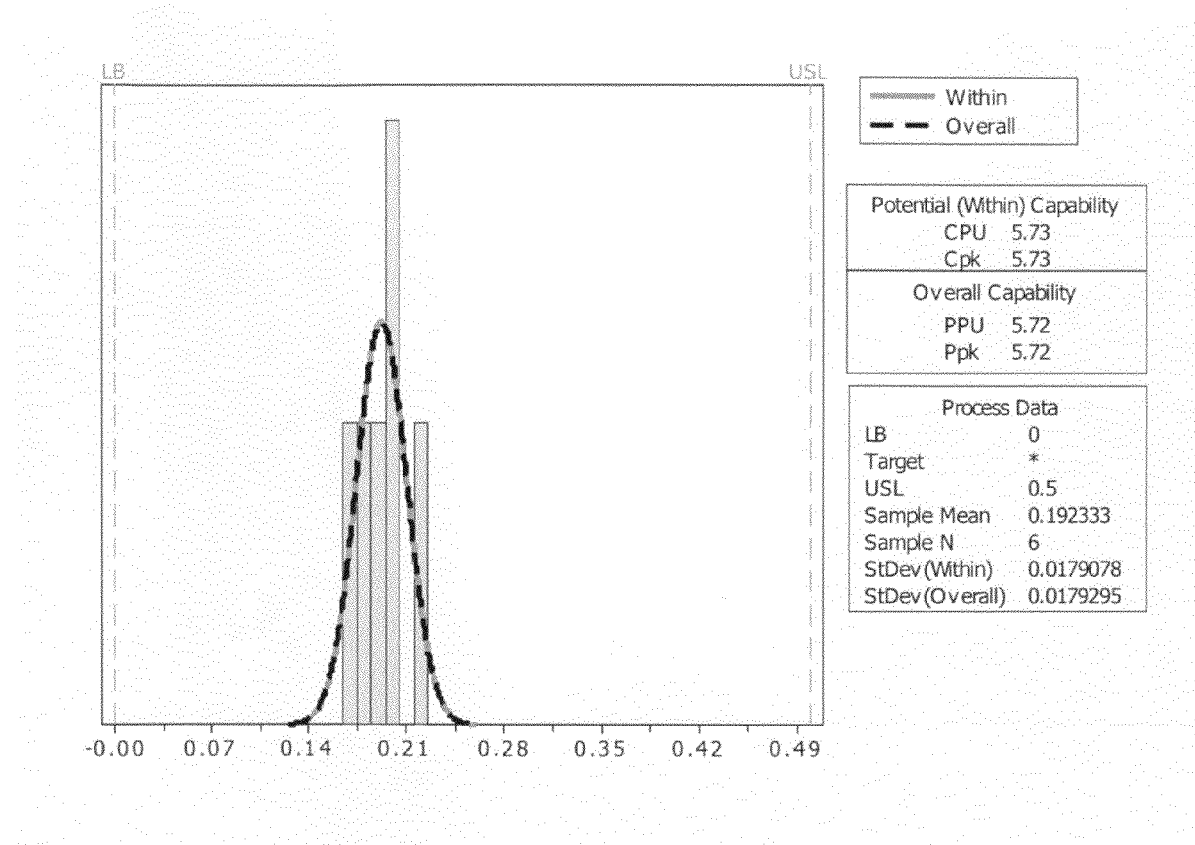
FIG. 2 illustrates that seeding of the process further reduces the β-epimer levels. Presented on the left is a process capability analysis in which the wt % β-epimer is plotted for 6 pilot plant runs. The process capability indexes (i.e., Cpk, Ppk) and other indices are presented on the right.

The invention provides an efficient synthetic route for the production of opiate alkaloids in a one-pot process via a cyclo-addition reaction between an opiate compound comprising a conjugated diene and a dienophile. It has been discovered that use of a solvent system comprising water in the process reduces the formation of impurities, such as the 7-β epimer of 6,14-endo-etheno-7α-acetyltetrahydro-thebaine. The solvent system generally comprises a combination of water and one or more other solvents that are miscible in water. As illustrated in FIG. 1, addition of water to the reaction of thebaine with methyl vinyl ketone significantly reduces the amount of impurity formed (i.e., the 7-β epimer of 6,14-endo-etheno-7α-acetyltetrahydro-thebaine). For example, addition of approximately 25% (v/v) of water to the solvent comprising isopropyl alcohol in the aforementioned reaction results in a 50% to 80% decrease in the amount of 7-β epimer formed compared to when the solvent comprises pure isopropyl alcohol. In addition to reducing the amount of impurities formed, it has been found that use of a solvent system comprising water results in a reaction product that more readily crystallizes upon cooling, thus eliminating the need to remove the dienophile (e.g., methyl vinyl ketone), which is extremely hazardous to handle. It has also been discovered that addition of a trace amount of seed material to the reaction mixture while it is cooling further reduces the amount of impurity formed. As described in Example 2, addition of a 0.001 Kg of seed material to a reaction mixture comprising 20 Kg of thebaine, methyl vinyl ketone and a solvent containing water resulted in an 88% reduction in the amount of 7-β epimer formed. The alkaloids produced by the process of the invention are typically intermediate compounds that may be utilized to produce a variety of biologically active alkaloids including buprenorphine and diprenorphine.

(I) Synthesis of Compounds Comprising Formula (II)

The process of the invention comprises a cyclo-addition reaction between an opiate compound comprising a conjugated diene, namely a compound comprising Formula (I), and a dienophile in the presence of a solvent system comprising water to produce an opiate alkaloid comprising Formula (II). This reaction is generally known as a Diels Alder reaction. For purposes of illustration, Reaction Scheme 1 depicts production of compound comprising Formula (II) in accordance with one aspect of the invention:

Reaction Scheme I

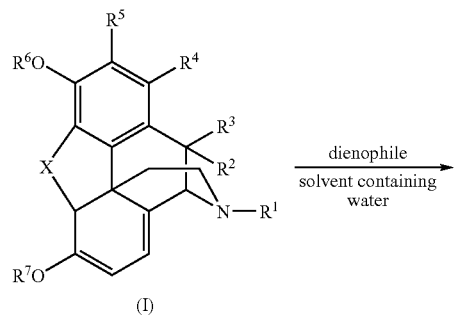

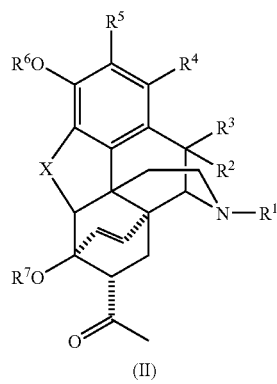

wherein:
  $R^1$ and $R^8$ are independently selected from the group consisting of hydrocarbyl and substituted hydrocarbyl;
  $R^2$ and $R^3$ are independently selected from the group hydrogen, hydrocarbyl and substituted hydrocarbyl;
  $R^4$ and $R^5$ are independently selected from the group consisting of hydrogen, hydrocarbyl, substituted hydrocarbyl, halogen, {—}OH, {—}NH$_2$, {—}SH, {—}SR$^8$, and {—}OR$^8$;
  $R^6$ and $R^7$ are independently selected from the group consisting of hydrogen, a protecting group, hydrocarbyl, and substituted hydrocarbyl; and
  X is a heteroatom.

In one exemplary embodiment, the compound comprising Formula (II) is 6,14-endo-etheno-7α-acetyltetrahydro-thebaine or a derivative of 6,14-endo-etheno-7α-acetyltetrahydro-thebaine comprising Formula (IIa):

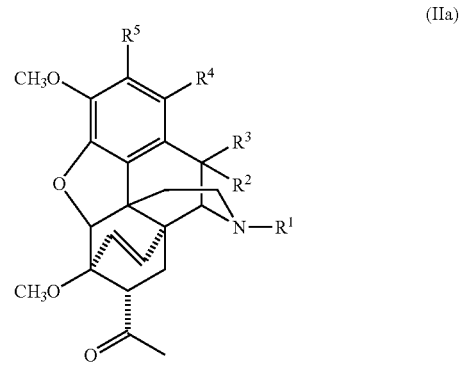

wherein:
  $R^1$, $R^2$, $R^3$, $R^4$, and $R^5$ are as defined for compounds comprising Formula (II). In an exemplary embodiment, the compound of Formula (IIa) is 6,14-endo-etheno-7α-acetyltetrahydro-thebaine (i.e., when $R^1$ is methyl, and $R^2$, $R^3$, $R^4$, and $R^5$ are hydrogen).

In yet another exemplary embodiment, the compound comprising Formula (II) is 6,14-endo-etheno-7α-acetyltetrahydro-oripavine or a derivative of 6,14-endo-etheno-7α-acetyltetrahydro-oripavine comprising Formula (IIb):

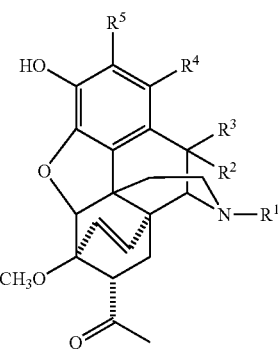

(IIb)

wherein:
R$^1$, R$^2$, R$^3$, R$^4$, and R$^5$ are as defined for compounds comprising Formula (II). In an exemplary embodiment, the compound of Formula (IIb) is 6,14-endo-etheno-7α-acetyltetrahydro-oripavine (i.e., when R$^1$ is methyl, and R$^2$, R$^3$, R$^4$, and R$^5$ are hydrogen).

(a) Reaction Mixture

The process commences with formation of a reaction mixture by combining a compound comprising Formula (I), with a dienophile in the presence of a solvent system comprising water. A variety of compounds having Formula (I) are suitable for use in the process. In one iteration of the process, for the compound having Formula (I), R$^1$ is an alkyl or substituted alkyl, R$^2$, R$^3$, R$^4$, and R$^5$ are hydrogen, and X is oxygen. In an alternative iteration, R$^6$ is methyl, and R$^7$ is methyl. In still another alternative iteration, R$^6$ is hydrogen and R$^7$ is methyl.

In one exemplary embodiment of the process, the compound comprising Formula (I) is thebaine or a thebaine derivative comprising Formula (Ia):

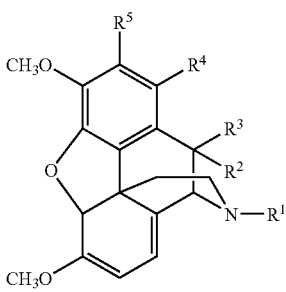

(Ia)

wherein:
R$^1$, R$^2$, R$^3$, R$^4$, and R$^5$ are as defined for compounds comprising Formula (I). In an exemplary embodiment, the compound of Formula (Ia) is thebaine (i.e., when R$^1$ is methyl, and R$^2$, R$^3$, R$^4$, and R$^5$ are hydrogen). In the process, when the compound of Formula (Ia) comprises thebaine then the resulting product is 6,14-endo-etheno-7α-acetyltetrahydro-thebaine.

In an alternative embodiment of the process, the compound comprising Formula (I) is oripavine or an oripavine derivative comprising Formula (Ib):

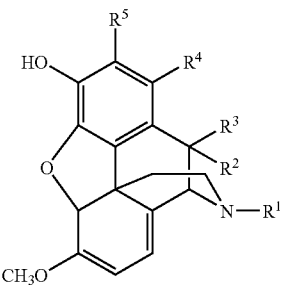

(Ib)

wherein:
R$^1$, R$^2$, R$^3$, R$^4$, and R$^5$ are as defined for compounds comprising Formula (I). In an exemplary embodiment, the compound of Formula (Ib) is oripavine (i.e., when R$^1$ is methyl, and R$^2$, R$^3$, R$^4$, and R$^5$ are hydrogen). In the process, when the compound of Formula (Ib) comprises oripavine then the resulting product is 6,14-endo-etheno-7α-acetyltetrahydro-oripavine.

In addition to a compound comprising Formula (I), the reaction mixture also comprises a dienophile. Typically, the dienophile is an α,β-unsaturated electron deficient dienophile. An exemplary dienophile is methyl vinyl ketone. Other suitable dienophiles include but are not limited to maleic anhydride, methyl acrylate, diethyl fumarate, benzoquinone, acetylene, 4-phenyl-1,2,4-triazolin-3,4-dione, and 2-methylpropenal. The molar ratio of the compound comprising Formula (I) to dienophile can and will vary. Typically, the molar ratio is from about 1:1.5 to about 1:5.5. In a preferred embodiment, the molar ratio of the compound comprising Formula (I) to dienophile is from about 1:1.75 to 1:3.

The reaction mixture, as detailed herein, also includes a solvent system comprising water. As shown in the examples, inclusion of water within an optimized range minimizes the formation of impurities, and in particular, the β-epimer of either 6,14-endo-etheno-7α-acetyltetrahydro-thebaine or 6,14-endo-etheno-7α-acetyltetrahydro-oripavine. As such, the solvent may comprise at least 5%, 10%, 15%, 20%, 25%, 30%, 35%, 40%, 45%, 50%, 55%, 60%, 65%, 70%, 75%, 80%, 85%, 90%, 95%, or 100% water. While it is envisioned that the solvent could comprise 100% water, typically at least one additional solvent is included. Suitable solvents to combine with water preferably include water miscible solvents. Suitable examples of water miscible solvents include but are not limited to alcohols, glyme, glycol, THF, DMF, NMP, and pyridine. In an exemplary embodiment, the solvent will comprise water and at least one alcohol. The arrangement of carbon atoms comprising the alcohol may be linear, branched or combinations thereof. Exemplary alcohols include methanol, ethanol, isopropanol, n-propanol, isobutanol, t-butanol, n-butanol, and combinations thereof. In a preferred embodiment, the solvent will comprise from about 10% to about 35% by weight water with the balance being alcohol.

(b) Reaction Conditions and Addition of Seed Material

In general, the reaction may be conducted at a temperature that ranges from about 50° C. to about 100° C. for a period of time that is sufficient to convert a substantial portion of the compound comprising Formula (I) to the compound comprising Formula (II). In a preferred embodiment, the temperature of the reaction may range from about 75° C. to about 85° C.

The reaction is preferably performed under ambient pressure, and preferably in an inert atmosphere (e.g., nitrogen or argon).

Typically, the reaction is allowed to proceed for a sufficient period of time until the reaction is complete, as determined by chromatography (e.g., HPLC). In this context, a "completed reaction" generally means that the reaction mixture contains a significantly diminished amount of compounds comprising either Formula (I), (Ia) or (Ib) and a significantly increased amount of compounds comprising Formula (II), (IIa) or (IIb) compared to the amounts of each present at the beginning of the reaction. Typically, the amount of compounds comprising Formula (I), (Ia) or (Ib) remaining in the reaction mixture may be less than about 0.01%.

When the reaction is completed, the reaction mixture is cooled. Typically, as detailed in the Examples, the reaction mixture is cooled from the reaction temperature (i.e., around 80° C.) to about room temperature then to about 5° C. As the reaction mixture is cooled, the compound comprising Formula (II), (IIa), or (IIb) typically crystallizes out of the reaction mixture. The reaction mixture at this point comprises the solvent, unreacted compounds of Formula (I) and dienophile. Since the product crystallizes out directly after the one-pot reaction, the compound comprising Formula (II) may be easily separated from the reaction mixture without solvent distillation. This beneficially avoids the need to handle the reaction mixture comprising the dienophile in order to isolate the reaction product.

It has been discovered that addition of seed material to the reaction mixture as it cools further reduces the amount of impurities formed. The seed material typically comprises a crystalline form of the compound comprising Formula (II). In addition, the seed material also typically comprises a very low percentage by weight of the target impurity, such as below about 0.5% by weight. The amount of seed material added can and will vary, but addition of even trace amounts (such as a single crystal) may reduce the target impurity. In one exemplary iteration, the compound comprising Formula (I) is thebaine, the compound comprising Formula (II) is 6,14-endo-etheno-7α-acetyltetrahydro-thebaine, and the target impurity to be minimized is the 7-β epimer of 6,14-endo-etheno-7α-acetyltetrahydro-thebaine. In this iteration, by way of non limiting example, 0.001 Kg of seed material comprising crystalline 6,14-endo-etheno-7α-acetyltetrahydro-thebaine may be added per every 20 Kg of thebaine charged to the reaction mixture. The seed material may be added as the reaction is cooling, such as for example, when the reaction is cooled to about 45° C. As illustrated in the examples, use of this seeding protocol in combination with a solvent system comprising water may reduce the amount of the 7-β epimer by as much as 90% by weight.

The yield of the compound comprising Formula (II) may vary. Typically, the yield of the compound may range from about 70% to about 95%. In one embodiment, the yield of the compound may range from about 70% to about 80%. In another embodiment, the yield of the compound may range from about 80% to about 90%. In a further embodiment, the yield of the compound may be greater than 90%.

In an exemplary embodiment, when the compound of Formula (I) is thebaine or oripavine and product of the process is 6,14-endo-etheno-7α-acetyltetrahydro-thebaine or 6,14-endo-etheno-7α-acetyltetrahydro-oripavine, then the amount of the 7-β epimer formed is less than about 1% by weight of the product (i.e., the compound comprising Formula (II)). In another embodiment, the amount of the 7-β epimer formed is less than about 0.75% by weight of the product. In yet another embodiment, the amount of the 7-β epimer formed is less than about 0.5% by weight of the product. In still another embodiment, the amount of the 7-β epimer formed is less than about 0.25% by weight of the product. In an exemplary embodiment, the amount of the 7-β epimer formed is less than about 0.2% by weight of the product. Stated another way, preferably the about of the 7-α epimer formed is typically greater than 99% by weight of the product, more typically, is greater than about 99.5% by weight of the product, and in an exemplary embodiment, the amount of the 7-α epimer formed is greater than about 99.8% by weight of the product.

(II) Synthesis of Compounds Comprising Formula (III)

Any of the compounds comprising Formulas (II) may be subjected to hydrogenation to form a compound comprising Formula (III). The hydrogenation may be achieved by methods commonly known in the art, such as by contacting the compounds comprising Formulas (II) with water or a proton donor under suitable reaction conditions according to Reaction Scheme 2:

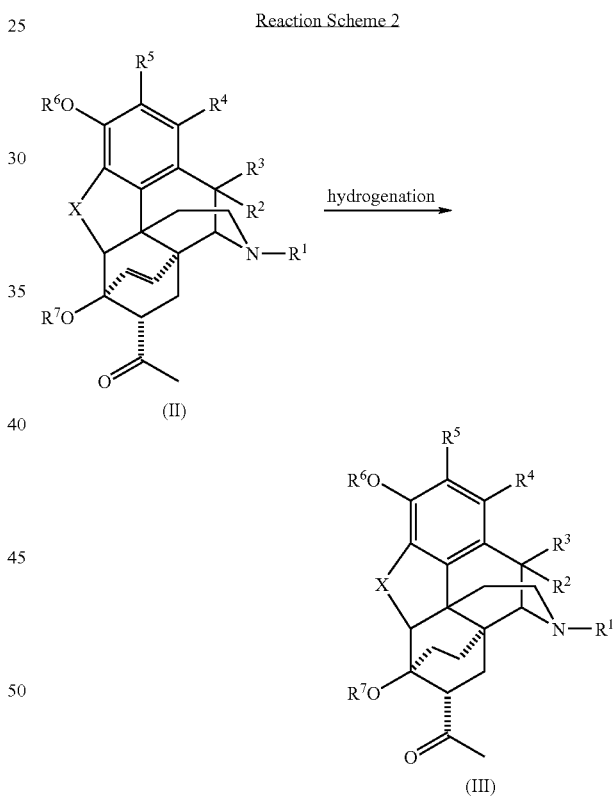

wherein:
$R^1, R^2, R^3, R^4, R^5, R^6, R^7$, and X are as described above for compounds having Formula (II).

The compounds comprising any of Formulas (I), (II), or (III) may have a (−) or (+) with respect to the rotation of polarized light based on whether the starting material used are in the (−) or (+) opiate absolute form. More specifically, each chiral center may have an R or an S configuration. The compounds formed by the processes of the invention comprise morphinans. For purposes of illustration, the ring atoms of a morphinan compound are numbered as diagrammed below.

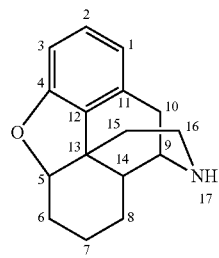

Some compounds described herein, such as compounds comprising Formula (II), may have at least six chiral centers, namely carbons C5, C6, C7, C9, C13, and C14.

The invention also encompasses use of pharmaceutically acceptable salts of any of the compounds described herein. Exemplary salts include without limitation: hydrochloride, hydrobromide, phosphate, sulfate, methansulfonate, acetate, formate, tartaric acid, maleic, malic, citrate, isocitrate, succinate, lactate, gluconate, glucuronate, pyruvate, oxalate, fumarate, propionate, aspartate, glutamate, benzoate, methyl fluoride, methyl chloride, methyl bromide, methyl iodide, and the like.

Definitions

The compounds described herein may have asymmetric centers. Compounds of the present invention containing an asymmetrically substituted atom may be isolated in optically active or racemic form. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention.

The term "acyl," as used herein alone or as part of another group, denotes the moiety formed by removal of the hydroxy group from the group COOH of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted homo- or heterocyclic aromatic groups. These aromatic groups are preferably monocyclic, bicyclic, or tricyclic groups containing from 6 to 14 atoms in the ring portion. The term "aromatic" encompasses the "aryl" and "heteroaryl" groups defined below.

The term "aryl" or "Ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The terms "halogen" or "halo" as used herein alone or as part of another group refer to chlorine, bromine, fluorine, and iodine.

The term "heteroatom" shall mean atoms other than carbon and hydrogen.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described below. Exemplary substituents include one or more of the following groups: hydrocarbyl, substituted hydrocarbyl, hydroxy, protected hydroxy, acyl, acyloxy, alkoxy, alkenoxy, alkynoxy, aryloxy, halogen, amido, amino, cyano, ketals, acetals, esters and ethers.

The term "heteroaryl" as used herein alone or as part of another group denote optionally substituted aromatic groups having at least one heteroatom in at least one ring, and preferably 5 or 6 atoms in each ring. The heteroaryl group preferably has 1 or 2 oxygen atoms and/or 1 to 4 nitrogen atoms in the ring, and is bonded to the remainder of the molecule through a carbon. Exemplary heteroaryls include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl and the like. Exemplary substituents include one or more of the following groups: hydrocarbyl, substituted hydrocarbyl, hydroxy, protected hydroxy, acyl, acyloxy, alkoxy, alkenoxy, alkynoxy, aryloxy, halogen, amido, amino, cyano, ketals, acetals, esters and ethers.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, aryloxy, hydroxy, protected hydroxy, acyl, acyloxy, nitro, amino, amido, nitro, cyano, ketals, acetals, esters and ethers.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

Having described the invention in detail, it will be apparent that modifications and variations are possible without departing from the scope of the invention defined in the appended claims.

EXAMPLES

The following examples illustrate various iterations of the invention.

Example 1

Preparation of 6,14-Endo-etheno-7α-acetyltetrahydro-thebaine

Under nitrogen, 575 g of wet technical grade thebaine (72 wt % by assay=414.11 g; 1.329 moles; 28% w/w water) was suspended by agitation in 1 L of isopropanol (ACS grade). Then, 264 mL of 90% methyl vinyl ketone (~2.2 equiv) and 200 mL of water were added to the mixture. The total water in the mixture is equal to thebaine-derived water+water added [(574×0.28=161 mL)+200 mL=361 mL; ~26% v/v relative to the total solvent: isopropanol+total water=~1361 mL]. The mixture was then gently warmed to reflux (79°-80° C.) over a period of 4 hours using an efficient condenser with a scrubber to minimize loss of methyl vinyl ketone vapors. The reaction was slightly exothermic but not self-sustaining. The mixture was then heated at 79°-80° C. for 14 hours. (After about 1 hour at reflux, the heterogeneous slurry became homogeneous.)

The reaction mixture was cooled to room temperature over a period of about 4 hours, then cooled to 5° C. and held at this temperature for 4 hours (the red/brown solution crystallized on cooling to give a yellow-colored suspension). There was typically a 4-5° C. heat of crystallization observed in a mantle but only about 1° C. observed in a jacketed reactor. The solid was filtered and washed with 5° C. isopropanol (2×100 mL) to give product as a white crystalline solid. The mother liquors (which typically contained about 6% yield of product) were discarded as hazardous waste.

The solid product was dried under vacuum (about 22" Hg) for about 12 hours to give 464.99 g of white crystalline solid. Secondary drying was done in a vacuum oven at about 22" Hg and 60° C. for about 12 hours (with appropriate traps) if the product (464.65 g; 91.58%, m.p. 118-120 ° C.) was to be stored. HPLC of the solid product typically assayed at greater than 99 wt % of product, about 0.32-0.73 wt % of the 7-β epimer, and less than 0.0087 wt % of un-reacted thebaine.

Example 2

Preparation of 6,14-Endo-etheno-7α-acetyltetrahydro-thebaine with Seeding 6,14-Endo-etheno-7α-acetyltetrahydro-thebaine was prepared essentially as detailed above in Example 1 except that seed crystals of 6,14-endo-etheno-7α-acetyltetrahydro-thebaine (1 g per 20 kg of thebaine) were added at 45° C. when the reaction was cooling. The assay values were similar except that the 7-β epimer levels were consistently about 0.19 wt %.

What is claimed is:

1. A process for the preparation of a compound of Formula (II):

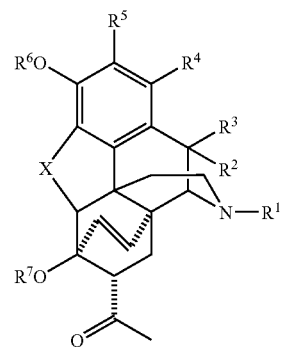

(II)

the process comprising:
(a) forming a reaction mixture by combining a compound of Formula (I), with a dienophile and a solvent comprising an alcohol and at least 10% water, wherein the compound of Formula (I) is:

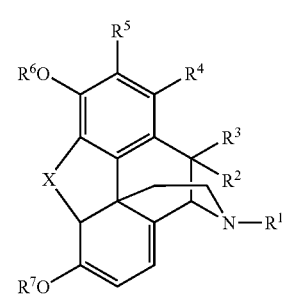

(I)

and
(b) heating the reaction mixture to form a compound of Formula (II), wherein:
$R^1$ and $R^8$ are independently selected from the group consisting of hydrocarbyl and substituted hydrocarbyl;
$R^2$ and $R^3$ are independently selected from the group hydrogen, hydrocarbyl and substituted hydrocarbyl;
$R^4$ and $R^5$ are independently selected from the group consisting of hydrogen, hydrocarbyl, substituted hydrocarbyl, halogen, {—}OH, {—}NH$_2$, {—}SH, {—}SR$^8$, and {—}OR$^8$;
$R^6$ and $R^7$ are independently selected from the group consisting of hydrogen, a protecting group, hydrocarbyl, and substituted hydrocarbyl; and
X is oxygen.

2. The process of claim 1, wherein the solvent comprises from about 10% to 35% (v/v) of water.

3. The process of claim 1, wherein the dienophile is methyl vinyl ketone; the molar ratio of the compound of Formula (I) to dienophile is from about 1:1.5 to about 1:5.5; and the reaction mixture is heated to a temperature of about 50° C. to about 100° C. for a period time that is sufficient for the conversion of a substantial portion of the compound of Formula (I) to the compound of Formula (II).

4. The process of claim 1, wherein:
R², R³, R⁴, and R⁵ are hydrogen;
R⁶ is selected from the group consisting of {—}CH₃, and hydrogen;
R⁷ is {—}CH₃; and
X is oxygen.

5. The process of claim 1, wherein a seed material comprising a crystalline form of the compound of Formula (II) is added to the reaction mixture as the reaction mixture is cooled to a temperature of about 5° C.

6. The process of claim 1, wherein the amount of α-epimer formed at C(7) is greater than about 99.5% by weight of the amount of compound of Formula (II); and the amount of β-epimer formed at C(7) is less than about 0.50% by weight of the amount of compound of Formula (II).

7. The process of claim 1, wherein the dienophile is methyl vinyl ketone and wherein:
R², R³, R⁴, and R⁵ are hydrogen;
R⁶ is selected from the group consisting of {—}CH₃, and hydrogen;
R⁷ is {—}CH₃; and
X is oxygen.

8. The process claim 1, further comprising subjecting the compound of Formula (II) to hydrogenation to form a compound of Formula (III):

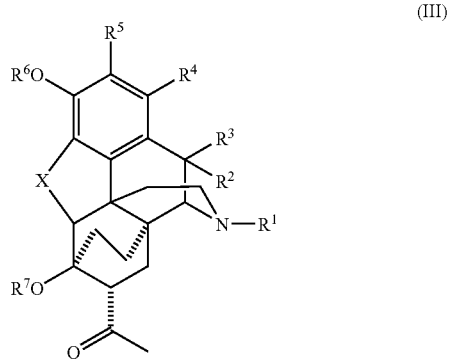

(III)

wherein:
R¹, R², R³, R⁴, R⁵, R⁶, R⁷, and X are as defined in claim 1.

9. A process for the preparation of a compound of Formula (IIa):

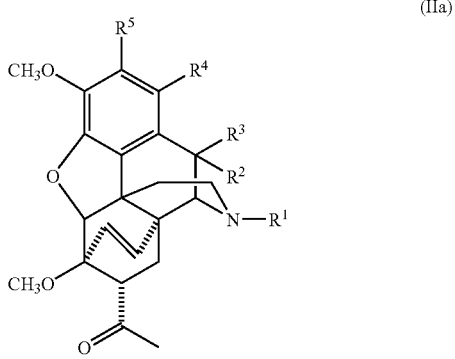

(IIa)

the process comprising:
(a) forming a reaction mixture by combining a compound of Formula (Ia), with a dienophile and a solvent comprising an alcohol and at least 10% water, wherein the compound of Formula (Ia) is:

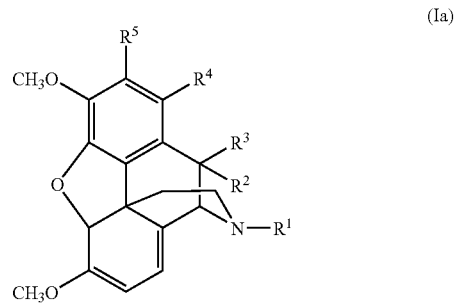

(Ia)

and
(b) heating the reaction mixture to form a compound of Formula (IIa), wherein:
R¹ and R⁸ are independently selected from the group consisting of hydrocarbyl and substituted hydrocarbyl;
R² and R³ are independently selected from the group hydrogen, hydrocarbyl and substituted hydrocarbyl; and
R⁴ and R⁵ are independently selected from the group consisting of hydrogen, hydrocarbyl, substituted hydrocarbyl, halogen, {—}OH, {—}NH₂, {—}SH, {—}SR⁸, and {—}OR⁸.

10. The process of claim 9, wherein the molar ratio of the compound of Formula (Ia) to dienophile is from about 1:1.75 to about 1:3: the reaction mixture is heated to a temperature of about 50° C. to about 100° C. for a period time that is sufficient for the conversion of a substantial portion of the compound of Formula (Ia) to the compound of Formula (IIa) and then the reaction mixture is cooled: and the solvent comprises from about 10% to 35% (v/v) of water.

11. The process of claim 10, wherein the dienophile is methyl vinyl ketone and R², R³, R⁴, and R⁵ are hydrogen.

12. The process of claim 11, further comprising adding seed material comprising a crystalline form of the compound having Formula (IIa) as the reaction mixture cools.

13. The process of claim 9, wherein the amount of β-epimer formed at C(7) is less than about 0.50% by weight of the amount of compound of Formula (IIa); and the amount of α-epimer formed at C(7) is greater than about 99.5% by weight of the amount of compound of Formula (IIa).

14. The process claim 9, further comprising subjecting the compound of Formula (IIa) to hydrogenation to form a compound of Formula (IIIa):

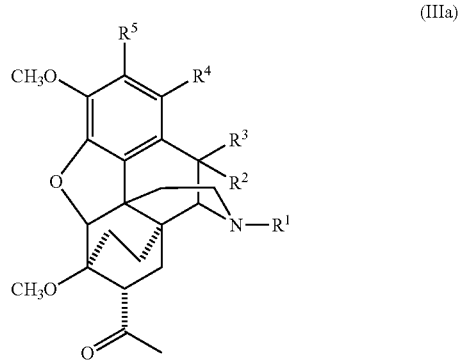

(IIIa)

wherein:

R¹, R², R³, R⁴, and R⁵ are as defined in claim 9.

15. A process for the preparation of a compound of Formula (IIb):

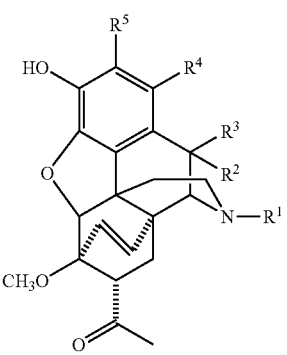

(IIb)

the process comprising:

(a) forming a reaction mixture by combining a compound of Formula (Ib), with a dienophile and a solvent comprising an alcohol and at least 10% water, wherein the compound of Formula (Ib) is:

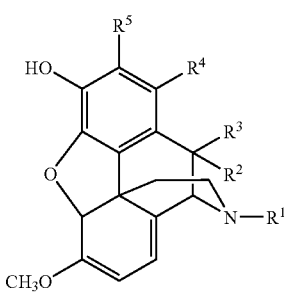

(Ib)

and (b) heating the reaction mixture to form a compound of Formula (IIb), wherein:

R¹ and R⁸ are independently selected from the group consisting of hydrocarbyl and substituted hydrocarbyl;

R² and R³ are independently selected from the group hydrogen, hydrocarbyl and substituted hydrocarbyl; and R⁴ and R⁵ are independently selected from the group consisting of hydrogen, hydrocarbyl, substituted hydrocarbyl, halogen, {—}OH, {—}NH₂, {—}SH, {—}SR⁸, and {—}OR⁸.

16. The process of claim 15, wherein the molar ratio of the compound of Formula (Ib) to dienophile is from about 1:1.75 to about 1:3 the reaction mixture is heated to a temperature of about 50° C. to about 100° C. for a period time that is sufficient for the conversion of a substantial portion of the compound of Formula (Ib) to the compound of Formula (IIb) and then the reaction mixture is cooled; and the solvent comprises from about 10% to 35% (v/v) of water.

17. The process of claim 16, wherein the dienophile is methyl vinyl ketone and R², R³, R⁴, and R⁵ are hydrogen.

18. The process of claim 16, further comprising adding seed material comprising a crystalline form of the compound having Formula (IIb) as the reaction mixture cools.

19. The process of claim 15, wherein the amount of β-epimer formed at C(7) is less than about 0.50% by weight of the amount of compound of Formula (IIb); and the amount of α-epimer formed at C(7) is greater than about 99.5% by weight of the amount of compound of Formula (IIb).

20. The process claim 15, further comprising subjecting the compound of Formula (IIb) to hydrogenation to form a compound of Formula (IIIb):

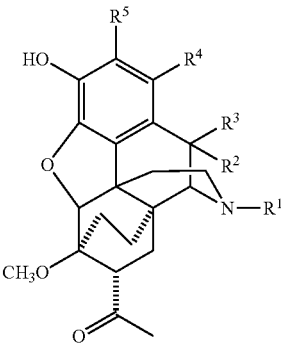

(IIIb)

wherein:

R¹, R², R³, R⁴, and R⁵ are as defined in claim 15.

* * * * *